United States Patent [19]

Hedger

[11] 4,190,461
[45] Feb. 26, 1980

[54] METHOD FOR REMOVING METALLIC SEEDS FROM NYLON TUBING USED IN INTERSTITIAL BRACHYTHERAPY

[75] Inventor: Bruce W. Hedger, Burbank, Calif.

[73] Assignee: Alpha-Omega Services, Inc., Paramount, Calif.

[21] Appl. No.: 890,572

[22] Filed: Mar. 20, 1978

[51] Int. Cl.² .............................................. B08B 3/12
[52] U.S. Cl. ......................................... 134/1; 134/42; 252/301.1 R; 424/1; 128/1.2
[58] Field of Search ................... 134/1, 38, 42; 424/1; 252/301.1 R; 128/1.2, 1.1; 209/1

[56] References Cited

U.S. PATENT DOCUMENTS

| | | | |
|---|---|---|---|
| 2,505,627 | 4/1950 | Pessel | 134/38 |
| 3,007,814 | 11/1961 | Bulat | 134/1 |
| 3,291,640 | 12/1966 | Livingston | 134/1 |
| 3,438,365 | 4/1969 | Packer et al. | 128/1.2 |
| 3,524,768 | 8/1970 | Miyashita et al. | 134/1 |
| 3,764,384 | 10/1973 | Berni | 134/38 |
| 3,975,208 | 8/1976 | Tate et al. | 134/38 |
| 4,070,203 | 1/1978 | Neisius et al. | 134/38 |

FOREIGN PATENT DOCUMENTS 837955  6/1960  United Kingdom ...................... 134/38

*Primary Examiner*—S. Leon Bashore
*Assistant Examiner*—George C. Yeung
*Attorney, Agent, or Firm*—Lyon & Lyon

[57] ABSTRACT

Described herein is a method for removing radioactive metal seeds from embedment in nylon. Nylon is added to a solvent to form a mixture comprising dissolved and undissolved nylon, solvent, and metallic seeds and the mixture is subjected to ultrasonic waves to substantially completely dissolve the nylon in the solvent, thus freeing up the metallic seeds. The solvent is decanted and the foregoing steps are repeated followed by adding acetone and decanting all resulting liquid. Finally the seeds are dried.

7 Claims, No Drawings

METHOD FOR REMOVING METALLIC SEEDS FROM NYLON TUBING USED IN INTERSTITIAL BRACHYTHERAPY

BACKGROUND OF THE INVENTION

Until recently, a woman, upon discovering that she had contracted breast cancer, had only one avenue open—mastectomy. Often, she would forego this radical surgery because of its traumatic consequences and the cancerous growth would continue unabated. Now, fortunately, victims of cancer particularly breast cancer may opt for an alternative, less drastic treatment. This revolutionary approach has been denominated interstitial brachytherapy and entails the temporary implantation of small particles of radioactive isotopes called seeds, in and around the cancerous tissue.

Interstitial brachytherapy had its genesis in 1901, shortly after the discovery of radium, when the Curies suggested that a small radium tube inserted into a tumor might produce beneficial consequences. The early pioneers in this area followed this suggestion but these crude methods required bulky radium tubes that were difficult to handle. In 1914 the technique was improved by the use of pure radium sulfate and the manufacturing of radium needles with steel or platinum. A similar method took advantage of the relatively short half-life of radon by collecting the gas in tiny glass tubes which were then inserted into the tumor for an indefinite period of treatment. However, it was soon discovered that the bare tubes produced necrosis due to the beta radiation emitted. One attempt to alleviate the harmful presence of beta radiation was to surround each glass tube with a few millimeters thickness of a bismuth paste. While this constituted some improvement, it was not until the radon was collected in gold capillary tubes instead of glass that there was successful filtration of these rays.

During the early 1920's it was discovered that certain types of cancers could be treated more effectively by radium needles of low intensities applied for a 6- to 10-day period. This produced good results in treating intraoral cancers. Later, rules were formulated which permitted a sound distribution of radium throughout the tumor and they enabled the radiotherapist to achieve a uniform dose within a ±10% range. Recently, radium substitutes have been developed and incorporated in the treatment and computerized dosimetry has become prevalent. Alternatives to radium that have received widespread implementation include Radon-222, Gold-198, Iridium-192, Iodine-125 and Cesium-137.

Interstititial implantation is chosen as the treatment where the cancers are not resected and where they are not so widespread, fast-growing or so highly radiosensitive to make external X-ray therapy or chemotherapy preferable. Interstitial brachytherapy can frequently be combined with other methods of treatment. It may be used in conjunction with surgery for implantation into a residual tumor, or with intracavity injection of radioactive material in intrathoracic and intraabdominal tumors. It also may be used with external radiation therapy. It often has been found that where part of the tumor is amenable to resection, the patient should undergo resection followed by implantation in the residual tumor. However, it is sometimes preferable to leave even an easily resectable tumor mass as a carrier for an implant.

Two types of implantation are possible—temporary or permanent. The temporary implant provides better control over the distribution of the radioactive sources and the dose. The temporary implant may be adjusted within wide limits after the implantation by the removing of radioactive sources at different times. Permanent implants are desirable for treating tumors in the abdominal and thoracic cavities.

Interstitial brachytherapy has been quite useful in the treatment of breast cancer. The implantation of radium needles covering the breat tumor, axilla, supraclavicular and intercostal spaces was described as early as 1935 by R. G. Hutchinson (Paterson, R. The Treatment of Malignant Disease by Radium and X-ray, Williams & Wilkins Co. (1st Ed. 1957)). This technique had to be abandoned, however, in view of the high incidence of brachial neuritis. A more limited radium implant for small breast tumors fixed to the chest wall was considered as an alternative to X-ray therapy.

The advance of megavoltage, external beam therapy following World War II, combined with a greater consciousness of the effects of radiation exposure, decreased the popularity of implants. However, interest in this form of treatment has undergone a resurgence as a means of avoiding radical surgery in some instances.

In examining the feasibility of employing interstitial brachytherapy, the size of the tumor must be considered. Where, for example, the breast tumor is relatively small, usually less than 4 cm., the doctors first excise the growth in a lumpectomy, a simple surgical procedure. Because removal of larger tumors would destroy the shape of the breast, these are left in place. Interstitial brachytherapy begins by pushing several hollow steel needles horizontally into the breast through the tumorous area so that they surface on the opposite side. Thin plastic tubes are threaded through the needles and anchored in place by small plastic buttons at either end. The radioactive material embedded in a thin nylon ribbon in the form of tiny seeds has been given a sheathing of, for example, stainless steel, platinum or tantalum to block dangerous ionizing beta rays but it permits the release of high energy gamma rays that will destroy the tumor. Preferably, the radiation treatment continues for three to five days. Similar techniques have been employed in treating other tumors as well, for example, those occurring in lips, oropharynx, retromola, trigone, base of the tongue and the palate.

While interstitial brachytherapy has made great inroads in cancer treatment and has become quite prevalent, some difficulties have been encountered in its operation. One of the prime problems faced relates to the recovery of the implanted radioactive seeds from the nylon ribbon. These seeds are generally expensive and it is advisable that they be reused whenever possible. While removal would not ordinarily engender any major difficulty, their radioactivity presents a handling problem.

The seeds may be inserted in the nylon ribbon by hand if they are not radioactive or by a suitable mechanical means. However, once they become radioactive, the removal of the seeds from the nylon by manual means is not possible because it subjects the technician to a prolonged exposure to deleterious rays. Mechanical means of removal do not solve the problem as they do not have the dexterity necessary for handling these small materials. It has been found that dissolving the nylon in a solvent to separate the seeds is also inadequate as the nylon forms a goopy mass further embedding the seeds rather than freeing up the seeds.

SUMMARY OF THE INVENTION

It is an object of this invention to provide a method for removing metallic seeds from a nylon ribbon by a means which lends itself to remote handling and is safe to employ with radioactive isotopes.

DESCRIPTION OF THE PREFERRED EMBODIMENT

It has been discovered that the goopy mass usually encountered when a solvent is added to nylon can be eliminated. The nylon-solvent mixture is subjected to cavitation in which the ultrasonic waves completely dissolve the nylon, thus freeing up the metallic seeds for reuse. In the preferred embodiment the radioactive seeds embedded in the nylon ribbons are placed in a solvent, usually phenol, however, it has been found that other solvents of nylon are equally suitable such as xylenol, formic acid and cresol. Phenol is preferred because it does not have the deleterious attributes found in, for example, cresol that may harm the operator.

The beaker is placed in a water bath containing a wetting agent, preferably soap, and the bath is transferred to an ultrasonic cleaner for treatment by the ultrasonic waves. A McMaster-Carr transistorized ultrasonic cleaner model 34100 K140, $5\frac{1}{2} \times 9\frac{1}{2}$ has been found to be quite satisfactory for this purpose. Once the ultrasonic cleaner begins operation, the cavitation causes the nylon tape to dissolve within about 8 to 12 minutes. In order to ensure proper removal of the nylon, the phenol is decanted and the treatment is repeated with fresh phenol. Upon completion of the second treatment, after the phenol is poured off, a solvent, such as acetone, is added. The acetone is removed and the seeds are permitted to dry. The seeds will then be free of nylon and suitable for reuse.

It is believed that the ultrasonic waves cause the phenomenon known as cavitation which is the formation of partial vacuums in a liquid. These partial vacuums, it is theorized, pit and wear away the solid surfaces when these vacuums collapse in the surrounding liquid. It is evident that this procedure lends itself to remote handling of the radioactive seeds, thus alleviating any difficulty that may occur due to the radioactive nature of the seeds.

While embodiments and applications of this invention have been shown and described, it will be apparent to those skilled in the art that many more modifications are possible without departing from the inventive concepts herein described. The invention, therefore, is not to be restricted except as is necessary by the prior art and by the spirit of the appended claims.

What is claimed is:

1. A method for recovering metallic seeds embedded in nylon which comprises the steps:
   a. adding nylon with radioactive metallic seeds embedded therein to a solvent in which nylon dissolves to form a mixture comprising dissolved and undissolved nylon, solvent, and metallic seeds; and
   b. subjecting the mixture to ultrasonic waves to substantially completely dissolve the nylon in the solvent, thus freeing up the metallic seeds.

2. A method according to claim 1 wherein the metallic seeds are radioactive.

3. A method according to claim 1 wherein the solvent is phenol.

4. A method according to claim 1 wherein the radioactive metallic seeds are embedded in a nylon ribbon.

5. A method according to claim 1 wherein the mixture is subjected to ultrasonic waves in an ultrasonic cleaner.

6. A method according to claim 5 wherein the mixture is subjected to ultrasonic waves for 8 to 12 minutes.

7. A method for removing radioactive metallic seeds from embedment in nylon, the method comprising:
   adding nylon with radioactive metallic seeds embedded therein to a solvent in which nylon dissolves to form a mixture comprising dissolved and undissolved nylon, solvent and metallic seeds;
   vibrating the mixture at ultrasonic frequencies to substantially completely dissolve the nylon in the solvent, thus freeing up the metallic seeds;
   decanting the solvent and repeating the foregoing steps of adding solvent and vibrating at ultrasonic frequencies; and
   thereafter adding acetone to the vibrated mixture, decanting substantially all resulting liquid and drying the seeds.

* * * * *